(12) United States Patent
Matou et al.

(10) Patent No.: US 12,310,714 B2
(45) Date of Patent: May 27, 2025

(54) CATHETER, GUIDE WIRE, OPENING POSITION IDENTIFICATION DEVICE, OPENING POSITION IDENTIFICATION METHOD, INTERNAL OBJECT PRESENCE DETERMINATION ASSISTANCE DEVICE, DIAGNOSTIC ASSISTANCE DEVICE, AND TREATMENT ASSISTANCE DEVICE

(71) Applicants: Takashi Matou, Tokyo (JP); Shinzo Tamada, Kumagaya (JP)

(72) Inventors: Takashi Matou, Tokyo (JP); Shinzo Tamada, Kumagaya (JP)

( * ) Notice: Subject to any disclaimer, the term of this patent is extended or adjusted under 35 U.S.C. 154(b) by 713 days.

(21) Appl. No.: 17/356,442

(22) Filed: Jun. 23, 2021

(65) Prior Publication Data

US 2022/0000386 A1    Jan. 6, 2022

Related U.S. Application Data

(63) Continuation of application No. PCT/JP2019/019016, filed on May 14, 2019.

(30) Foreign Application Priority Data

Dec. 27, 2018 (JP) ................. 2018-246344

(51) Int. Cl.
*A61B 5/06* (2006.01)
*A61M 25/00* (2006.01)
*A61M 25/09* (2006.01)

(52) U.S. Cl.
CPC ......... *A61B 5/061* (2013.01); *A61M 25/0074* (2013.01); *A61M 25/09* (2013.01);
(Continued)

(58) Field of Classification Search
CPC .......................... A61B 5/061; A61M 25/0074
See application file for complete search history.

(56) References Cited

U.S. PATENT DOCUMENTS

| 4,248,214 A | 2/1981 | Kish |
| 4,567,882 A * | 2/1986 | Heller ............. A61B 1/0625 |
| | | 128/207.14 |

(Continued)

FOREIGN PATENT DOCUMENTS

| CA | 2585858 A1 | 5/2006 |
| CN | 1853573 A | 11/2006 |

(Continued)

OTHER PUBLICATIONS

The extended European search report of the corresponding EP application No. 19903363.0 dated Jul. 14, 2022.

(Continued)

*Primary Examiner* — Oommen Jacob
(74) *Attorney, Agent, or Firm* — Muncy, Geissler, Olds & Lowe, P.C.

(57) ABSTRACT

A catheter, a guide wire, an opening position identification device, an opening position identification method, an internal object presence determination assistance device, a diagnostic assistance device, and a treatment assistance device that can easily identify the position of an opening of the catheter in a body are provided. A guide wire 20 is inserted into a catheter 30 having openings for introducing a fluid substance into the body, or for sucking the fluid substance in the body. One or more light sources 10 for identifying the positions of openings 32 of the catheter 30 are provided. The catheter 30 may be provided with one or more light sources 10 for identifying the positions of the openings 32 of the catheter 30.

15 Claims, 13 Drawing Sheets

(52) U.S. Cl.
CPC ............... *A61M 2210/1039* (2013.01); *A61M 2210/1078* (2013.01); *A61M 2210/1085* (2013.01)

(56) References Cited

U.S. PATENT DOCUMENTS

| | | | | |
|---|---|---|---|---|
| 7,300,429 | B2* | 11/2007 | Fitzgerald | A61B 5/0086 604/500 |
| 7,917,193 | B2* | 3/2011 | Crane | A61B 5/06 600/476 |
| 9,808,179 | B2* | 11/2017 | O'Dea | A61M 25/1018 |
| 2002/0133148 | A1* | 9/2002 | Daniel | A61B 18/1477 606/34 |
| 2005/0131510 | A1* | 6/2005 | Chen | A61N 5/062 607/122 |
| 2006/0036164 | A1 | 2/2006 | Wilson | |
| 2007/0287998 | A1* | 12/2007 | Sharareh | A61B 18/1492 606/41 |
| 2008/0194973 | A1* | 8/2008 | Imam | A61B 90/39 600/478 |
| 2012/0323089 | A1* | 12/2012 | Feer | A61J 15/0084 600/301 |
| 2014/0243640 | A1* | 8/2014 | O'Dea | A61B 5/1076 600/373 |
| 2016/0045101 | A1 | 2/2016 | Nakatate | |
| 2016/0184023 | A1* | 6/2016 | Grace | A61B 18/26 606/7 |
| 2016/0367168 | A1 | 12/2016 | Malinin | |
| 2019/0046417 | A1* | 2/2019 | Flexman | A61J 15/0088 |

FOREIGN PATENT DOCUMENTS

| | | |
|---|---|---|
| JP | S63-189258 U | 12/1988 |
| JP | 2008-518738 A | 6/2008 |
| JP | 2013-172855 A | 9/2013 |
| JP | 2013-544112 A | 12/2013 |
| JP | 2014-184061 A | 10/2014 |
| JP | 2014-188176 A | 10/2014 |
| JP | 2014-209930 A | 11/2014 |
| JP | 2017-099519 A | 6/2017 |
| JP | 2018-519046 A | 7/2018 |
| JP | W2018/207752 A1 | 5/2020 |
| JP | W2018/221404 A1 | 6/2020 |
| WO | 2006/049787 A2 | 5/2006 |
| WO | 2013171870 A1 | 11/2013 |
| WO | 2017/011085 A1 | 1/2017 |
| WO | 2018207753 A1 | 11/2018 |
| WO | 2018/221404 A1 | 12/2018 |

OTHER PUBLICATIONS

Office action of the corresponding CN application No. 201980086442 dated Dec. 28, 2022.
Office Action of the corresponding TW application No. 108116595 mailed Sep. 27, 2022.
International Search Report of PCT/JP2019/019016 mailed Jul. 9, 2019 and English Translation thereof.
International Preliminary Report on Patentability of PCT/JP2019/019016 issued Jun. 16, 2021, which includes Written Opinion of the International Searching Authority of PCT/JP2019/019016 mailed Jul. 9, 2019, and English translation thereof.
Office Action of the corresponding JP patent application No. 2020-523828 mailed Jun. 26, 2020 and English translation thereof.
Office Action of the corresponding JP patent application No. 2020-523828 mailed Aug. 13, 2020 and English translation thereof.
Office Action of the corresponding JP patent application No. 2020-523828 mailed Sep. 3, 2020 and English translation thereof.
Office action of the corresponding KR application No. 10-2021-7023699 mailed Jun. 4, 2024 and English translation thereof.
Office Action of the corresponding JP application No. 2020-210900 mailed Jun. 13, 2024 and English translation thereof.

* cited by examiner (A) (B)

(A) (B)

(A)

(B)

CATHETER, GUIDE WIRE, OPENING POSITION IDENTIFICATION DEVICE, OPENING POSITION IDENTIFICATION METHOD, INTERNAL OBJECT PRESENCE DETERMINATION ASSISTANCE DEVICE, DIAGNOSTIC ASSISTANCE DEVICE, AND TREATMENT ASSISTANCE DEVICE

TECHNICAL FIELD

The present invention relates to a catheter, a guide wire, an opening position identification device, an opening position identification method, an internal object presence determination assistance device, a diagnostic assistance device, and a treatment assistance device.

BACKGROUND ART

As methods of identifying the position of a catheter, the method of providing an electrode on the catheter, and identifying the position with the impedance of the electrode, the method of performing position identification by a magnetic position sensor, and the like have been proposed (refer to Patent Literature 1).

CITATION LIST

Patent Literature

Patent Literature 1: Japanese Translation of PCT International Application Publication No. 2018-519046

SUMMARY OF INVENTION

Technical Problem

An object of the present invention is to provide a catheter, a guide wire, an opening position identification device, an opening position identification method, an internal object presence determination assistance device, a diagnostic assistance device, and a treatment assistance device that can easily identify the position of an opening of the catheter in a body.

Solution to Problem

Although conventionally, it has not even recognized as a problem to identify the position of an opening of a catheter, the present inventors have found out that various problems can be solved by identifying the position of the opening of the catheter.

Also, the present inventors have found out the invention that can make it easy to grasp the position of an opening of a catheter. Specifically, while there was no idea of identifying the position of a light source provided in a catheter in a body by a photographing unit such as a camera, the present inventors have found out to grasp the position of the light source by the photographing unit, and have also found out that the position of the opening of the catheter can be identified through the position of the light source.

Further, the present inventors have found out that, when light is introduced through a catheter or an optical fiber from a light source outside the body, light loss is large, light diffusivity is low, and the amount of light is insufficient.

One aspect of a guide wire of the present invention is a guide wire to be inserted into a catheter having an opening for introducing a fluid substance into a body, or for sucking the fluid substance in the body, wherein the guide wire is provided with one or more light sources for identifying a position of the opening of the catheter.

One aspect of a catheter of the present invention is a catheter into which the guide wire of the present invention is inserted.

One aspect of the catheter of the present invention is a catheter having an opening for introducing a fluid substance into a body, or for sucking the fluid substance in the body, wherein the catheter is provided with one or more light sources for identifying a position of the opening of the catheter.

One aspect of the catheter of the present invention is a catheter, wherein when an end face of a tip of the catheter is opened, light is not emitted from the end face of the opened tip.

One aspect of an opening position identification device of the present invention can include the catheter of the present invention, and a photographing unit for photographing a light source of the catheter when the catheter is in a body.

One aspect of the opening position identification device of the present invention can include a display device that displays information based on image information or video information photographed by the photographing unit.

One aspect of the opening position identification device of the present invention can include a light receiving unit that receives light of the light sources of the catheter, when the catheter is in the body.

One aspect of the opening position identification device of the present invention includes a first information processing unit, wherein the first information processing unit can have a function of identifying whether or not a predetermined opening of the catheter is in a lung.

One aspect of the opening position identification device of the present invention includes a second information processing unit, wherein the second information processing unit can identify whether or not a predetermined opening of the catheter is below a diaphragm.

One aspect of the opening position identification device of the present invention includes a third information processing unit, wherein the third information processing unit can have a function of identifying whether or not a predetermined opening of the catheter is in a predetermined position or region of an alimentary canal.

One aspect of the opening position identification device of the present invention includes a fourth information processing unit, wherein the fourth information processing unit can have a function of identifying whether or not a predetermined opening of the catheter is in a predetermined position or region from a ureter to a bladder.

One aspect of a method of identifying a position of an opening of a catheter of the present invention can include a step of inserting the catheter described in the present invention into a body, a step of causing the light sources of the catheter to emit light, and a step of photographing light of the light sources by a photographing unit.

As one aspect of the method of identifying the position of the opening of the catheter of the present invention, a step of inserting the catheter described in the present invention into a body, a step of causing the light sources of the catheter to emit light, and a step of receiving light of the light sources by a light receiving unit can be included.

An object presence determination assistance device of the present invention is for assisting determination of whether or not an object exists in a predetermined portion or organ in a body, and includes the opening position identification device described in the present invention.

A diagnostic assistance device of the present invention includes the opening position identification device described in the present invention.

A treatment assistance device of the present invention includes the opening position identification device described in the present invention.

Here, the fluid substance is one that is fluid, and is a concept that includes a liquid, and a mixture of a liquid and a solid. It is assumed that in the body means in the body of a human being or an animal.

Advantageous Effects of Invention

According to the present invention, the absolute position of an opening of a catheter can be easily identified.

When discharging or sucking a fluid substance from the opening of the catheter, it is important whether or not the opening is in a predetermined position. When the opening of the catheter is not in an appropriate position, for example, when the opening of the catheter enters a lung, and a nutrient or a liquid material flows into the lung via the opening, although a problem occurs such as aspiration pneumonia, such a problem can be solved according to the present invention.

BRIEF DESCRIPTION OF DRAWINGS

FIG. 2 (B) is a diagram schematically showing a state at the time when the guide wire is inserted into the catheter.

FIG. 3 (B) is a diagram schematically showing a state at the time when a guide wire is inserted into the catheter.

FIG. 6 (B) is a diagram schematically showing a cross section along A1-A1 line in FIG. 6 (A).

FIG. 8 (B) is a diagram schematically showing a cross section along A2-A2 line in FIG. 8 (A).

DESCRIPTION OF EMBODIMENTS

Hereinafter, a preferred embodiment of the present invention is described in detail.

1. Guide Wire

Figure 1:
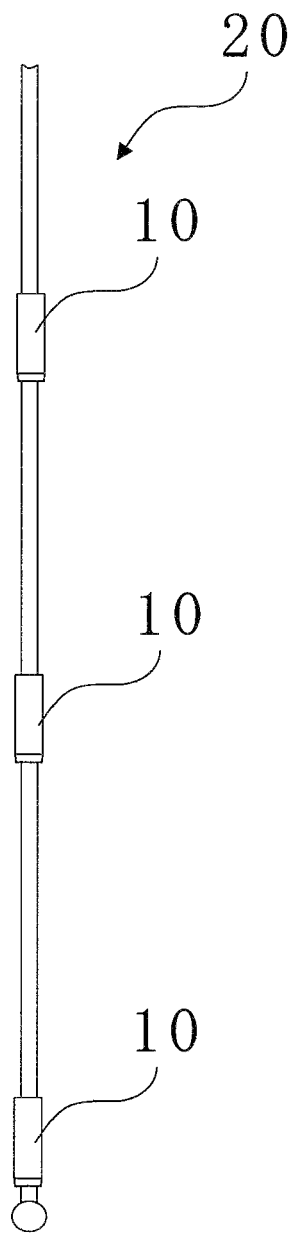
FIG. 1 is a diagram schematically showing a guide wire according to an embodiment.

A guide wire 20 according to an embodiment is inserted into a catheter 30, and is provided with light sources 10 as shown in FIG. 1.

Figure 2:
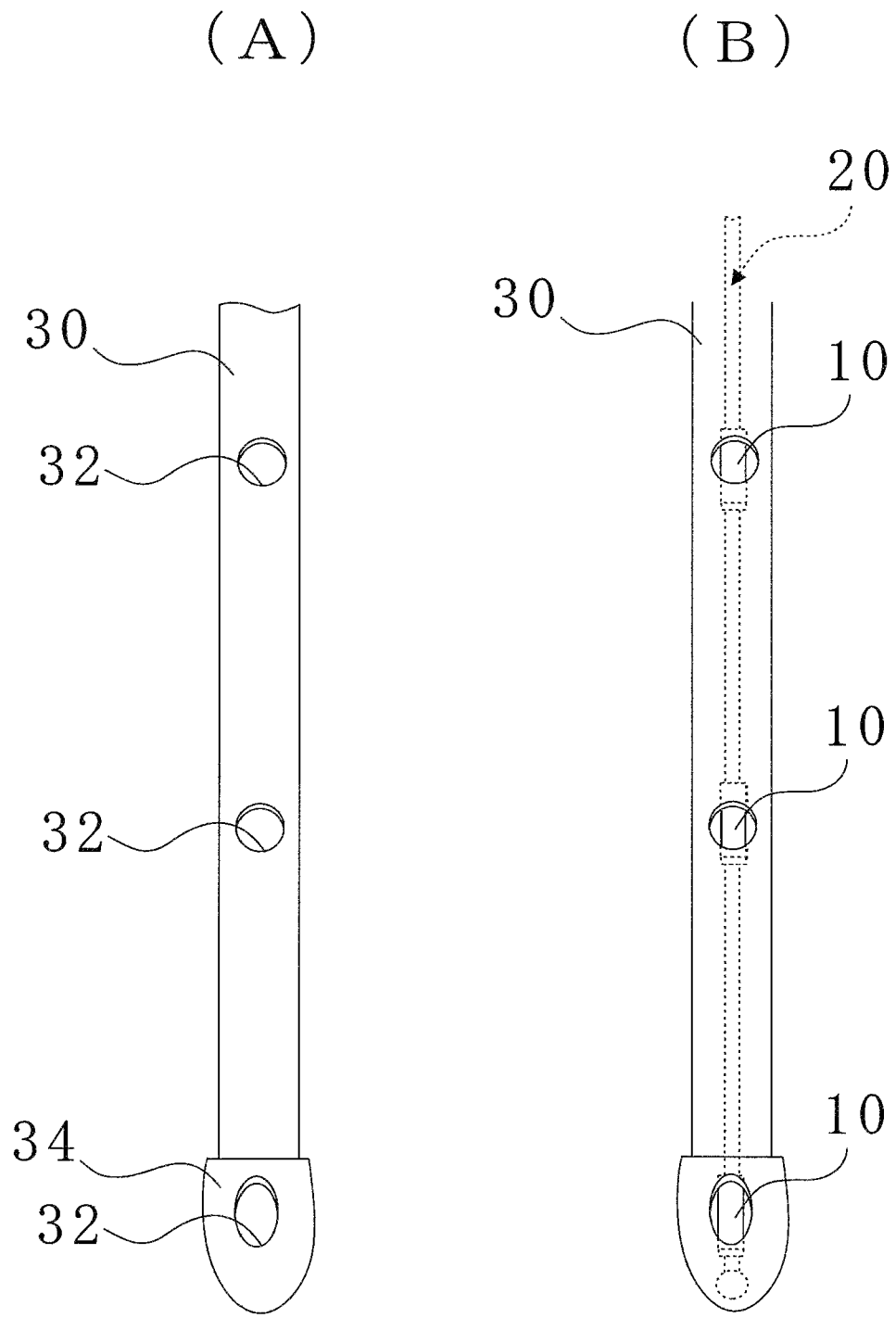
FIG. 2 (A) is a diagram schematically showing an example of a catheter into which the guide wire is to be inserted.
Figure 3:
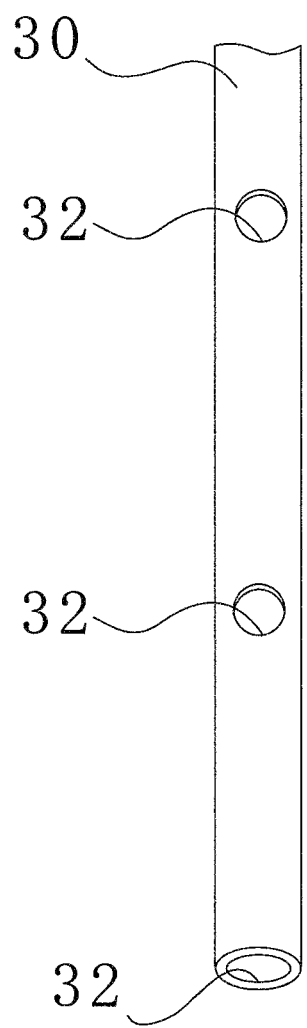
FIG. 3 (A) is a diagram schematically showing an example of a catheter.
Figure 3:
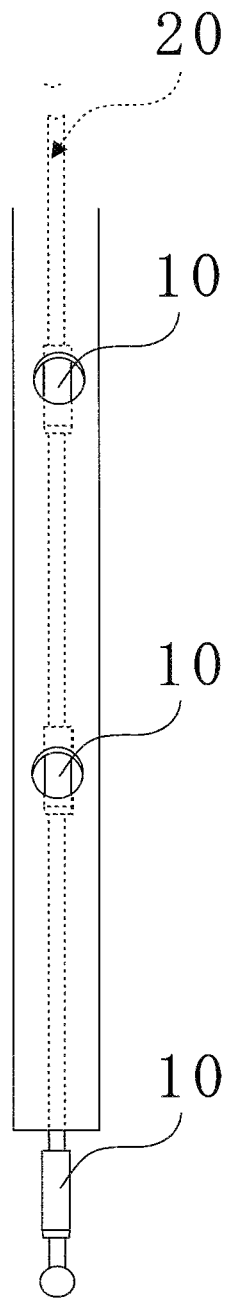
Figure 4:
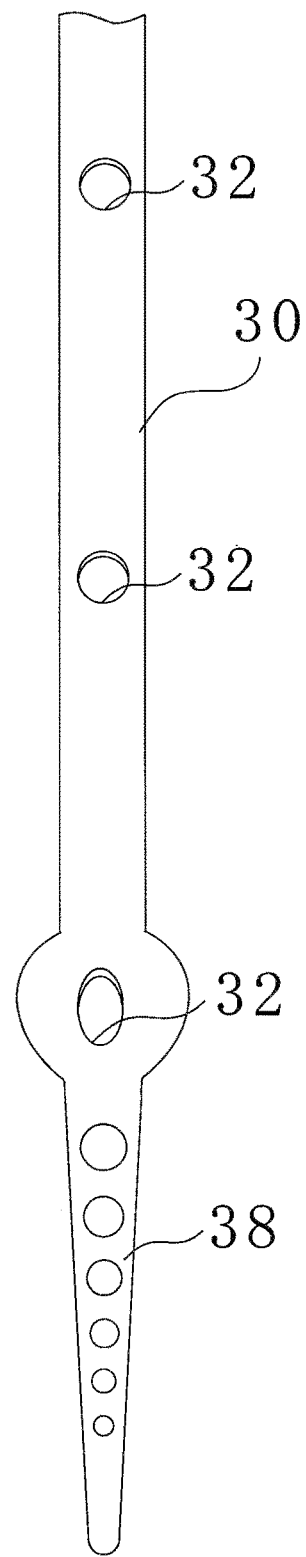
FIGS. 4 (A) and (B) schematically show examples of a catheter.
Figure 4:
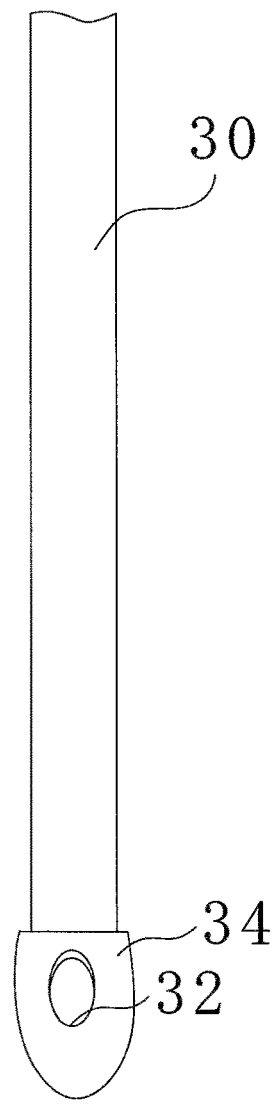

The catheter 30 can be the form as shown in FIG. 2 (A), FIG. 3 (A), or FIG. 4. The catheter 30 is provided with at least one opening 32 for introducing a fluid substance into a body, or for sucking the fluid substance in the body. As the fluid substance to be introduced into the body, for example, a nutrient, a medicine, and the like can be listed. As the fluid substance to be sucked from the body, for example, a gastric fluid and the like can be listed. The opening 32 of the catheter 30 may be provided in a side surface, and a tip may be provided to be an open end.

One or more light sources 10 can be provided in the guide wire 20. The light sources 10 are provided so as to correspond to the positions of the openings 32, when the guide wire 20 is inserted into the catheter 30. That is, the light sources 10 are set to the guide wire 20 in the positions where the light of the light sources 10 is emitted to the outside through the openings 32. Wiring (conducting wire) 36 can be provided to be bundled with the guide wire 20. Electricity can be supplied to the light sources 10 through the wiring 36.

An insertion facilitating member (olive) 34 having a stopper function for the guide wire 20 is provided at a tip of the catheter 30 shown in FIG. 2 (A). The opening 32 may be provided also in the insertion facilitating member 34. The catheter 30 shown in FIG. 3 (A) is in a form without the insertion facilitating member 34 for the guide wire 20 at the tip. FIG. 3 (B) schematically shows a state where the guide wire 20 is inserted into the catheter 30 in FIG. 3 (A). The catheter 30 shown in FIG. 4 (A) is in a form having a weight holding portion 38 that holds a weight on the tip side. Note that, as shown in FIG. 4 (B), the number of the openings 32 may be one. The light sources 10 may be provided in the catheters 30 shown in FIG. 2 to FIG. 4.

2. Catheter

Figure 5:
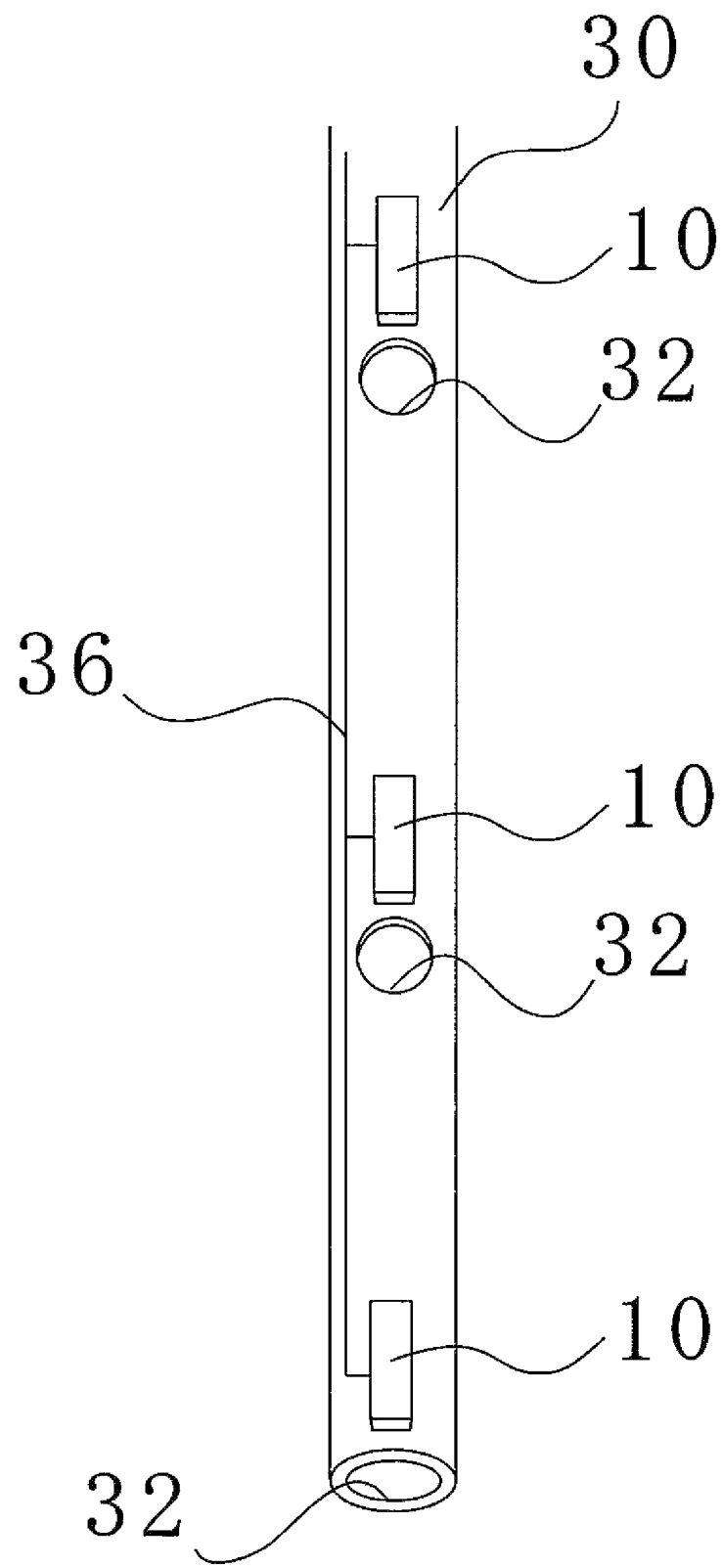
FIG. 5 is a diagram schematically showing a catheter according to the embodiment.

The catheter 30 according to the embodiment has the openings 32 for introducing the fluid substance into the body, or for sucking the fluid substance in the body. One or more light sources 10 for identifying the positions of the openings 32 of the catheter 30 are provided. Specifically, as shown in FIG. 5, the light sources 10 are provided in the positions corresponding to the openings 32 of the catheter 30. The light sources 10 may be provided in positions adjacent to each other in the axial direction in relation to the openings 32, or may be provided in portions of the catheter 30 that are located in the horizontal direction of the openings 32 of the catheter 30 (or the radial direction which is perpendicular to the axial direction). The wiring (conducting wire) 36 is provided in the catheter 30, and the light sources 10 are electrically connected to the wiring 36. By providing the wiring 36, the secondary effect is obtained that the catheter 30 can be easily inserted into a predetermined position by making the catheter 30 harder to break, while maintaining the elasticity of the catheter 30.

3. Light Sources and Implementation of Light Sources

Known light sources can be applied to the light sources 10, and the light sources 10 can be a LED light source such as a LED light bulb. The light of the light sources 10 is preferably the light that easily passes through the body, and can be, for example, near infrared ray.

Figure 6:
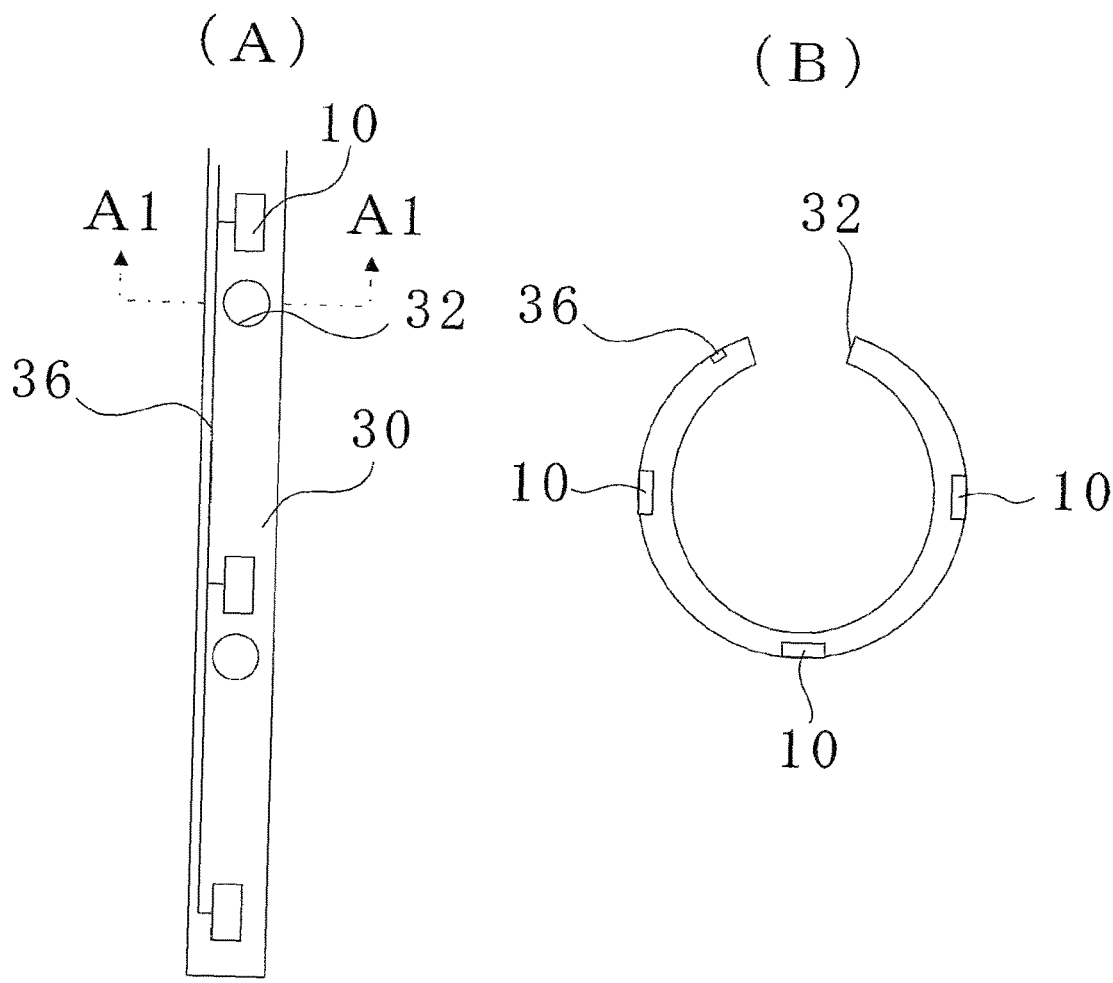
FIG. 6 (A) is a diagram schematically showing an example of implementing light sources to a catheter.

In FIG. 5, a form is shown in which the light sources 10 are placed on the catheter 30. In FIG. 6, a mode is shown in which the light sources 10 are embedded in the catheter 30. FIG. 6 (B) schematically shows a cross section along A1-A1 line in FIG. 6 (A). As shown in FIG. 6 (B), the light sources 10 may be provided in portions of the catheter 30 located in the horizontal direction of the opening 32 of the catheter 30, and may be provided to be fit into the catheter 30.

Figure 7:
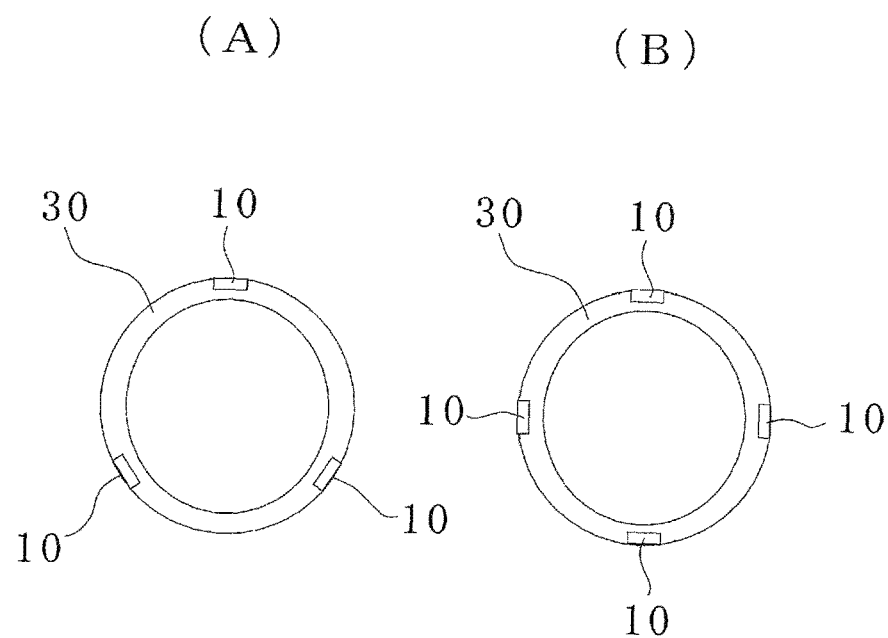
FIG. 7 is a diagram schematically showing examples of implementing light sources to a catheter.

As shown in FIG. 7, a plurality of (for example, three or four) light sources 10 may be provided not in the portions of the catheter 30 located in the horizontal direction of the opening 32 of the catheter 30, but in the circumference of the catheter 30 in positions adjacent to each other in the axial direction. By providing a plurality of light sources 10 in this manner, the light of the light sources 10 will be positively spread over a wider area centering on the axial direction.

Figure 8:
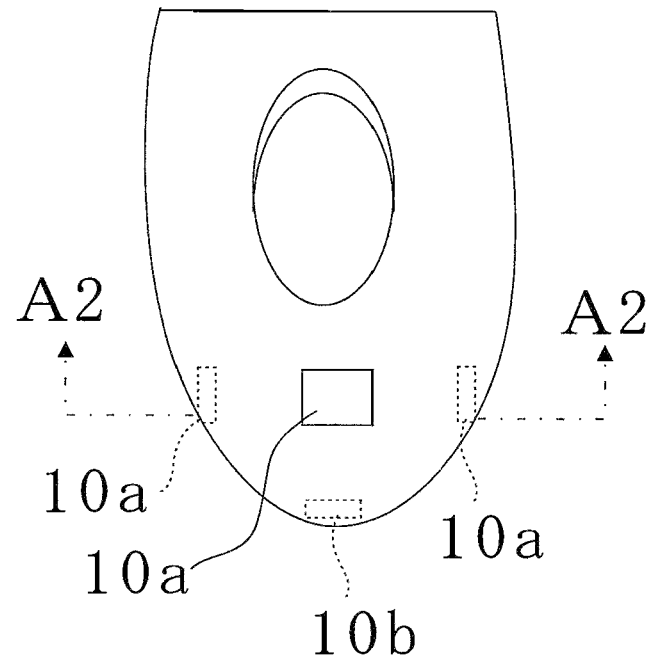
FIG. 8 (A) is a diagram schematically showing an example in which light sources are implemented in an insertion facilitating member of a catheter.
Figure 8:
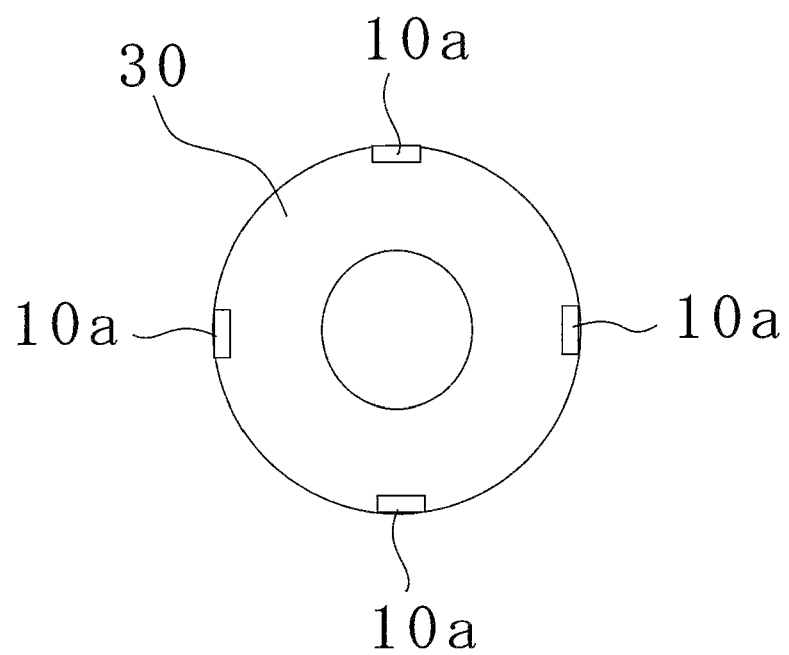

As shown in FIG. 8, the light sources 10 may be provided in the insertion facilitating member 34 for the catheter 30. A first light source 10a can be, for example, a light source that emits light in the horizontal direction with respect to the axial direction of the catheter 30. A second light source 10b can be a light source that emits light in the axial direction of the catheter 30. Accordingly, even if the body position or posture is changed, a photographing unit 42 can more positively photograph the light of the light sources 10.

Figure 9:
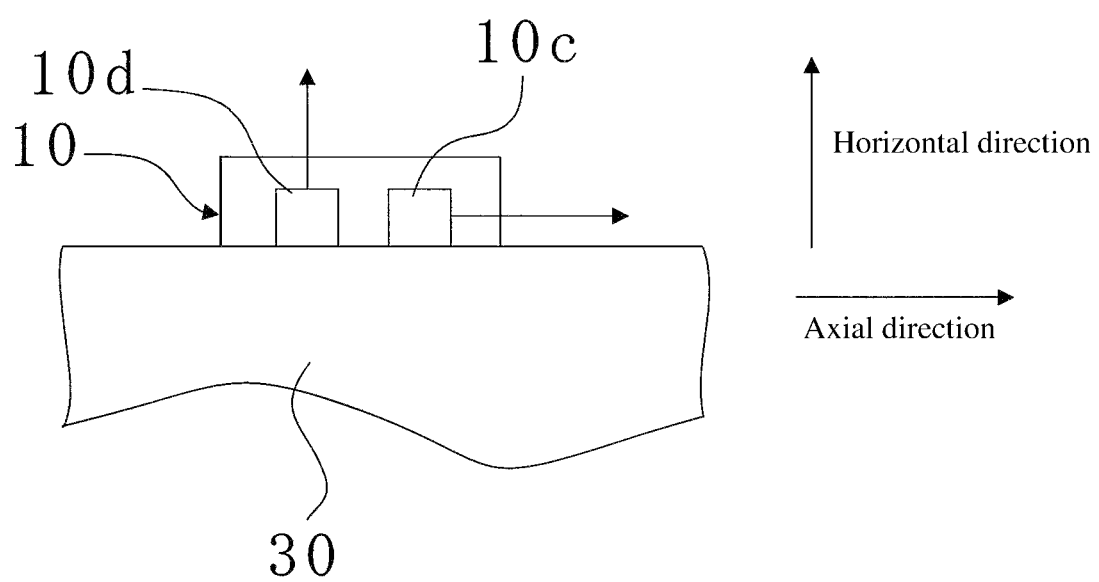
FIG. 9 is a diagram for describing the light emission directions of a light source.

As shown in FIG. 9, the light source 10 can also be configured to include a plurality of light emitting elements. Specifically, the light source 10 can include a light emitting element 10c that emits light in the axial direction, and a light emitting element 10d that emits light in a direction (for example, the horizontal direction) intersecting the axial direction. Additionally, a plurality of light sources 10 that emit light in the axial direction and a plurality of light sources 10 that emit light in a direction (for example, the horizontal direction) intersecting the axial direction may be provided. Accordingly, even if the body position or posture is changed, the photographing unit 42 can more positively photograph the light of the light sources.

By providing a plurality of light sources 10 for identifying the same opening 32, and changing the respective wavelengths of the plurality of light sources 10, it is possible to identify which direction the opening 32 faces.

A case is considered where the catheter 30 has a plurality of openings 32, and the light source 10 is provided for each of the plurality of openings 32. In that case, it is possible to identify which opening 32 is located in which position, by changing the wavelengths of the light of light sources 10 that identify the different openings 32.

4. Application Example of Catheter

As the catheter 30 according to the embodiment, for example, application examples in a tube from the mouth to the anus, a blood vessel including a cerebral blood vessel, a ureter, and a bladder can be considered.

Figure 10:
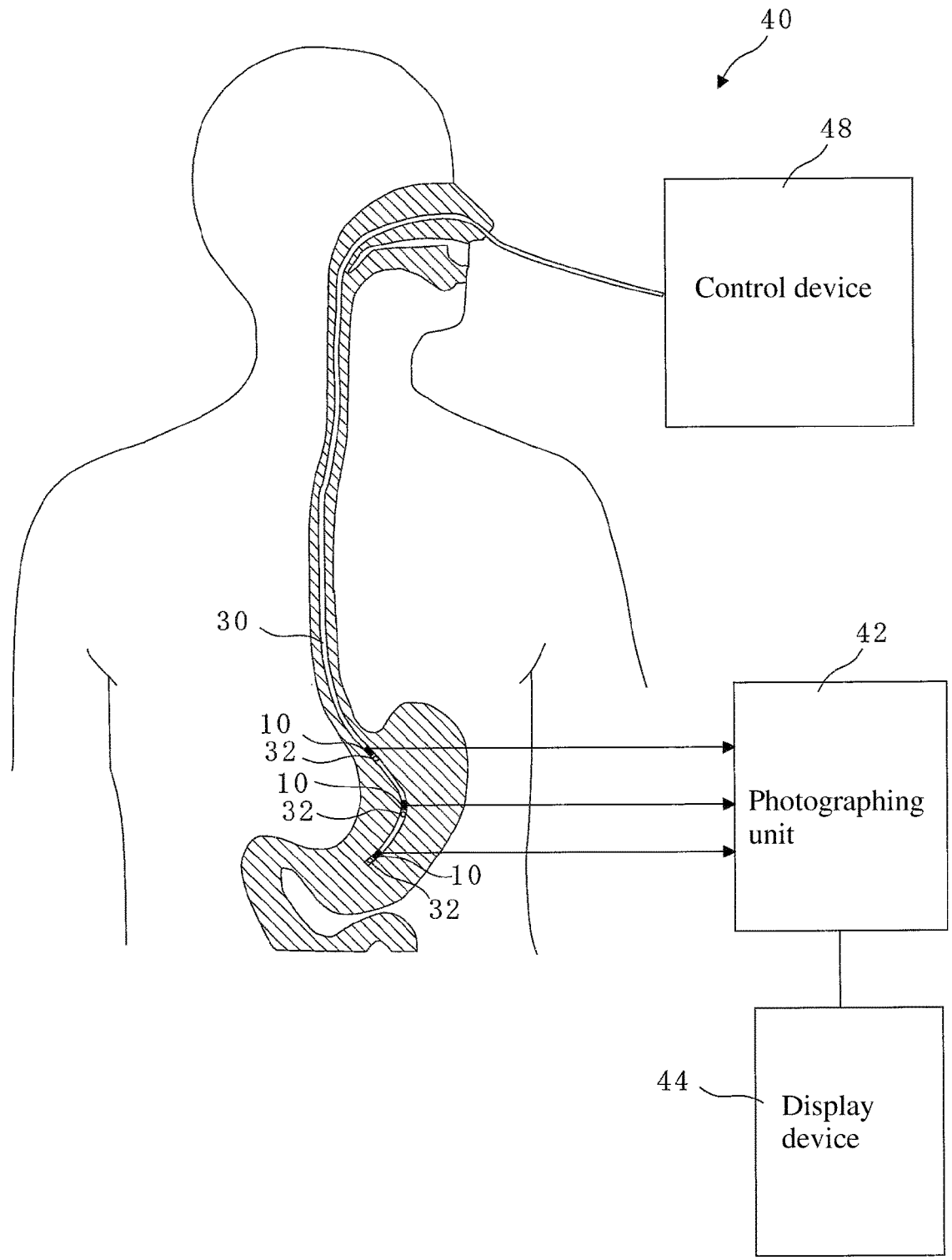
FIG. 10 is a diagram schematically showing an opening position identification device for identifying the positions of openings of a catheter.

5. Opening Position Identification Device and Opening Position Identification Method As shown in FIG. 10, an opening position identification device 40 for identifying the positions of the openings 32 of the catheter 30 can include the catheter 30 according to the embodiment, and the photographing unit 42 for photographing the light sources 10 of the catheter 30 when the catheter 30 is in the body. Here, it is assumed that the catheter 30 according to the embodiment includes the catheter 30 into which the guide wire 20 provided with the light sources 10 is inserted, and the catheter 30 provided with the light sources 10.

Figure 11:
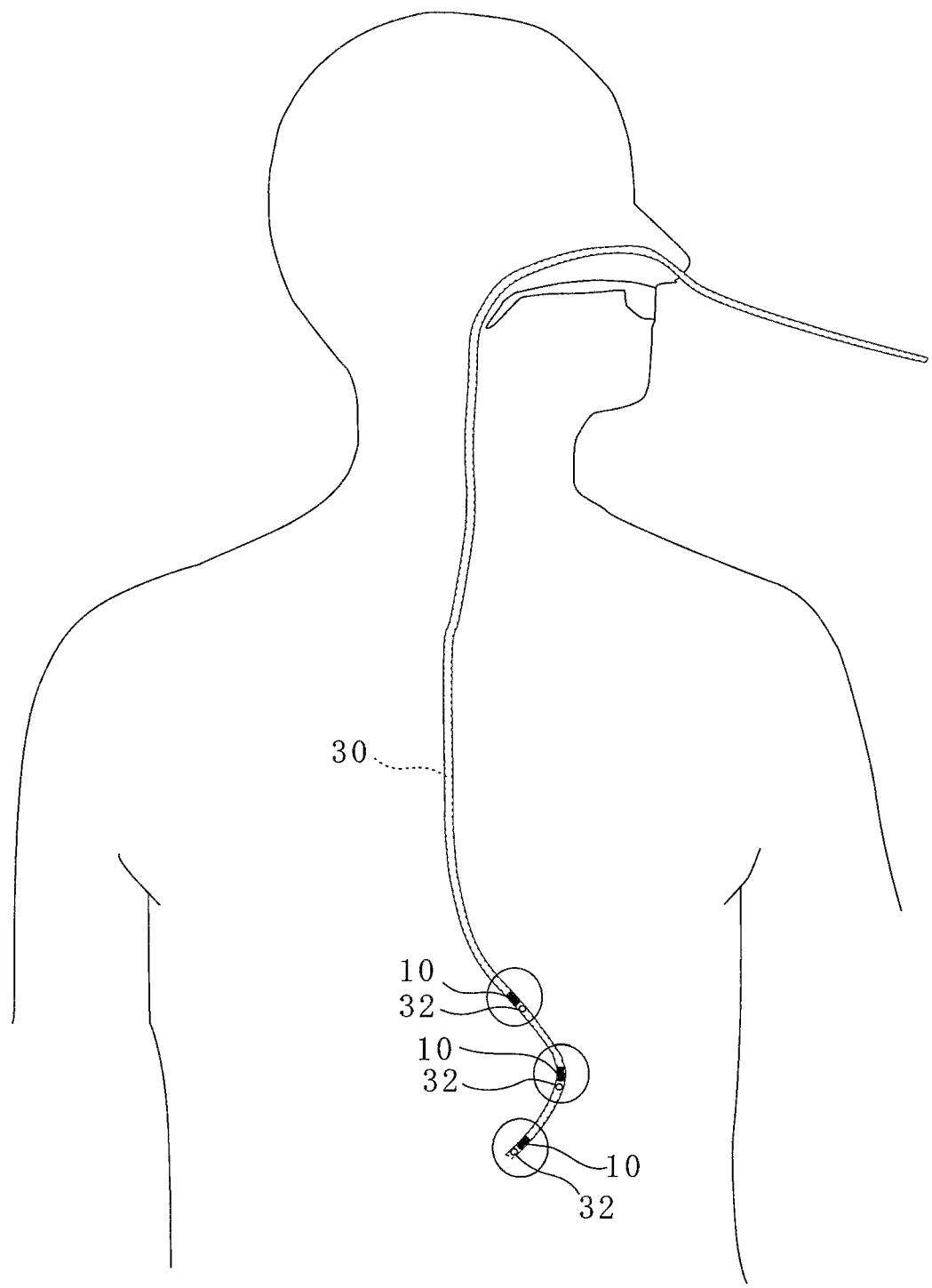
FIG. 11 is a diagram schematically showing a photographed image of light sources in a case where the light sources are photographed by a photographing unit of the opening position identification device for identifying the positions of the openings of the catheter.

The photographing unit 42 is not particularly limited as long as the light of the light sources 10 can be photographed, and a camera such as a CCD camera and a camera for astronomic observation can be applied. When the light sources 10 are light sources that emit near infrared rays, the photographing unit 42 can be a camera (including a digital camera) from which a filter for blocking near infrared ray is removed. When photographed by the photographing unit 42, a photographed image or a photographed video in which the portions of the light sources 10 are illuminated as shown in FIG. 11 can be obtained.

The opening position identification device 40 can include a display device that displays information based on image information or video information photographed by the photographing unit 42.

Figure 12:
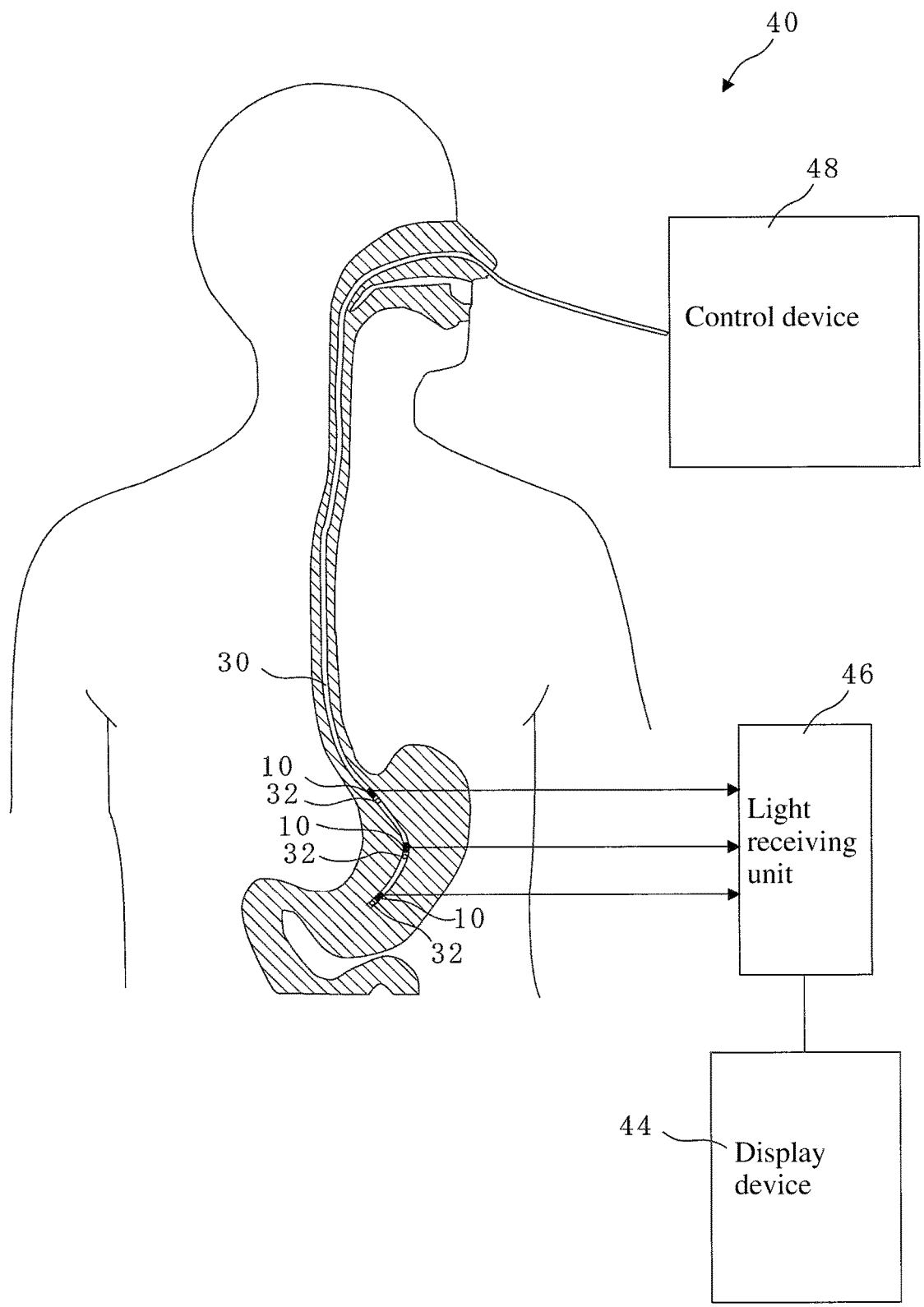
FIG. 12 is a diagram schematically showing the opening position identification device for identifying the positions of the openings of the catheter.

As shown in FIG. 12, the opening position identification device 40 can include a light receiving unit 46 that receives the light of the light sources 10 of the catheter 30, when the catheter 30 according to the embodiment is in the body. Although it is determined in relation to the light sources 10, when the light sources 10 are LED light sources, the light receiving unit 46 can be configured by, for example, a diode. The light receiving state of the light receiving unit 46 may be displayed on the display device.

Figure 13:
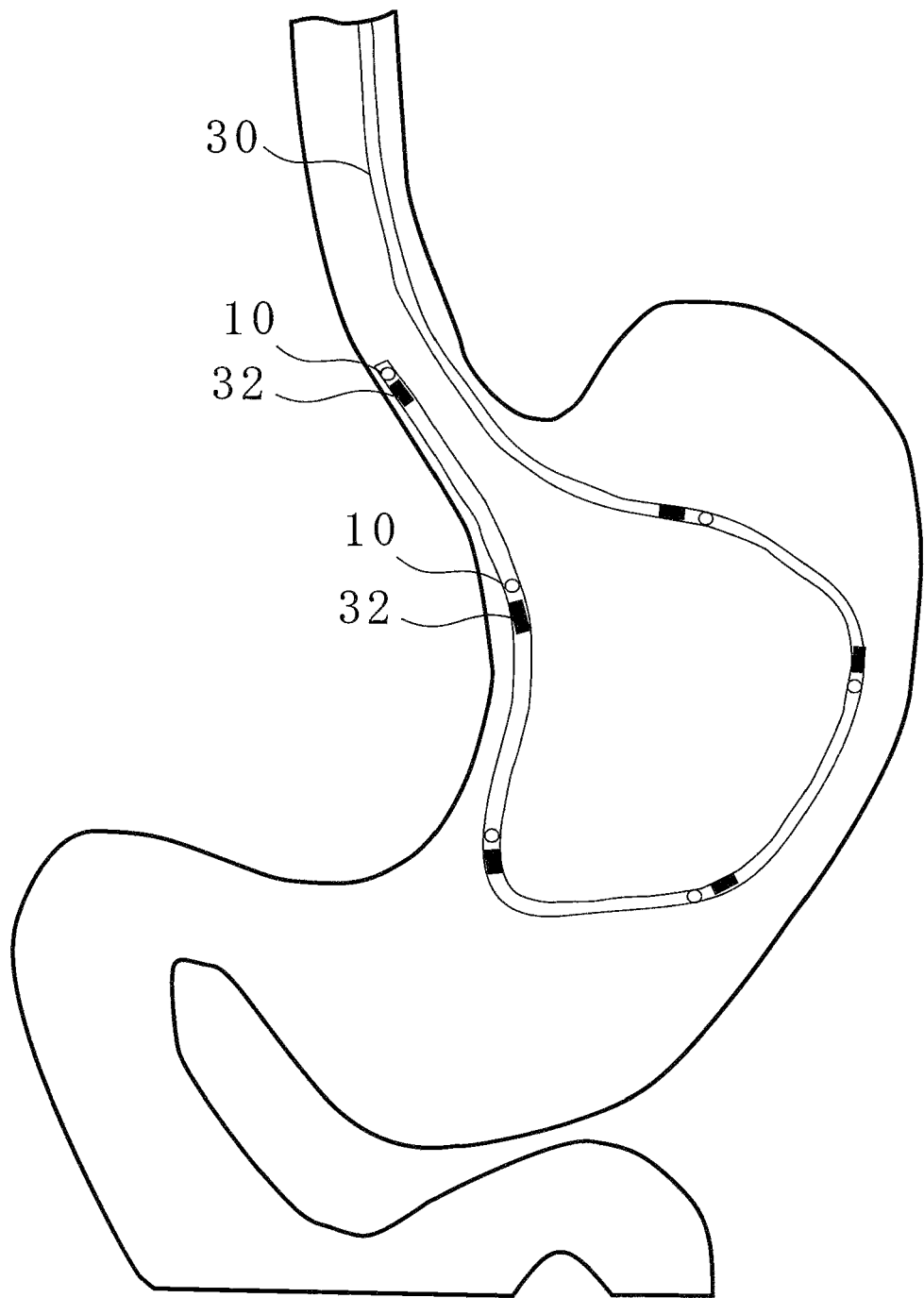
FIG. 13 is a diagram for describing the significance for identifying the positions of the openings of the catheter.
Figure 14:
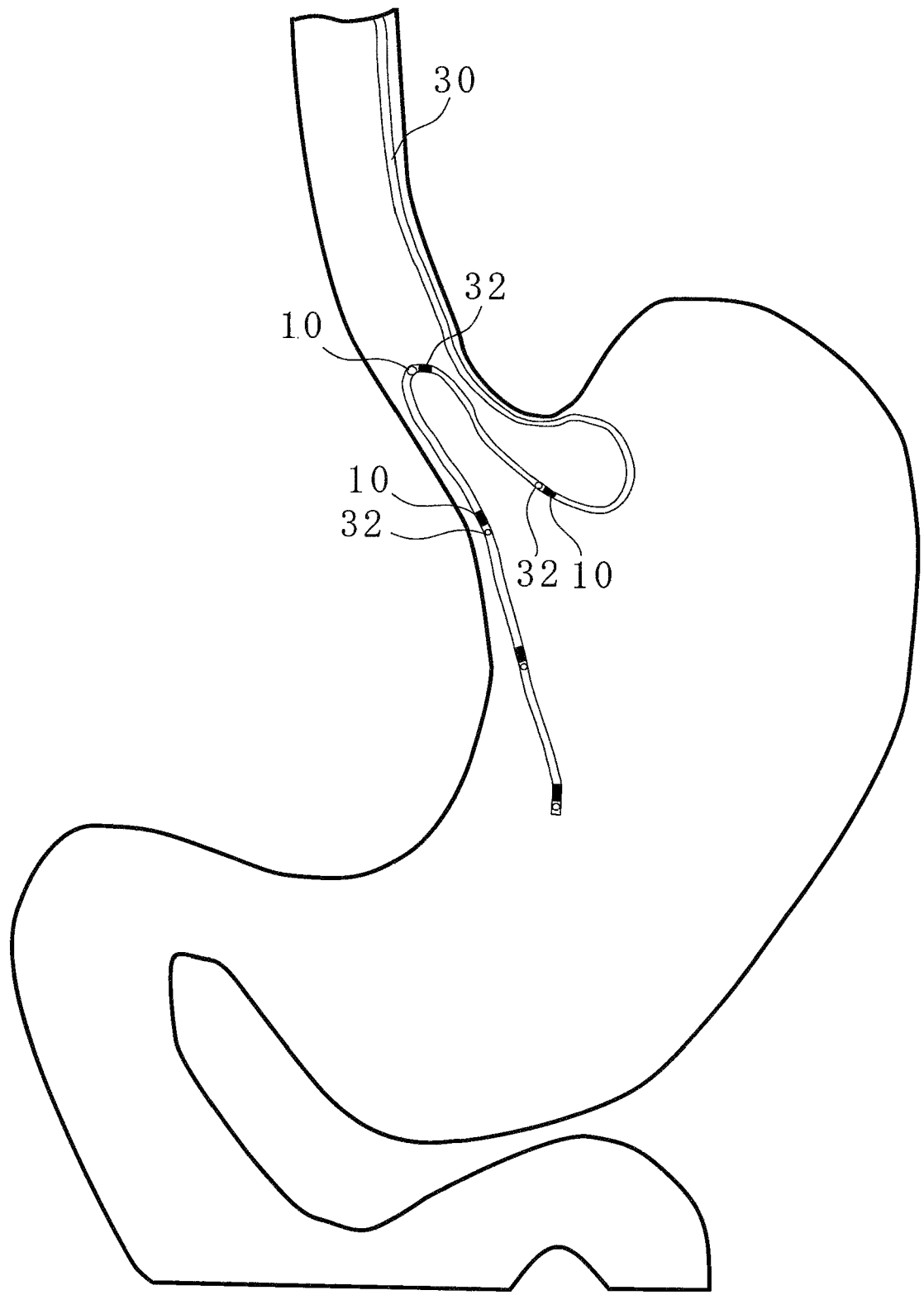
FIG. 14 is a diagram for describing the significance for identifying the positions of the openings of the catheter.

An example of the significance of identifying the positions of a plurality of openings 32 with a plurality of light sources 10 will be described by using FIG. 13 and FIG. 14. Taking a case where the catheter 30 is in the stomach for an example, when the catheter 30 has a plurality of openings 32, the positions of the openings 32 are not necessarily arranged sequentially from the top to the bottom from the rear end side toward the tip side. That is, even when the intermediate openings 32 are in the stomach, there are cases where the tip is above the cardia, and where two openings 32 are in the positions within the stomach, but the opening 32 between the two openings 32 is above the cardia. In such a case, it is possible to know in what mode the catheter 30 is in the stomach by photographing the light sources 10 by the photographing unit 42, and identifying the positions of openings 32.

The display device is not particularly limited as long as displaying is possible, and for example, a known display or the like can be applied.

The positions of predetermined portions and organs, such as the diaphragm and the lungs, may be displayed in a photographed image or video displayed on the display device. The positions of the diaphragm, the lungs, and the like may be recognized by the photographing unit 42, or may be grasped by another inspection device, for example, an X-ray device.

It is also possible to recognize the state of the catheter 30 in the body by photographing the light from a plurality of light sources 10 by the photographing unit 42, and displaying the photographed image on the display device. Additionally, it is also possible to focus on one light source 10, and to display the trajectory along which the light source 10 has moved on the display device, from the photographed information or light reception information. When the catheter 30 has a plurality of openings 32, the light source 10 is provided for each of the plurality of openings 32, and the wavelengths of the light of the light sources 10 that identify the different openings 32 are changed, it is possible to identify which opening 32 is in which position by recognizing the wavelength of the light by the photographing unit 42 or the light receiving unit 46.

The opening position identification device 40 can include an information processing unit. The information processing unit can have, for example, a first information processing unit to a fourth information processing unit as follows.

The first information processing unit has a function of identifying whether or not a predetermined opening 32 of the catheter 30 is in a lung.

The second information processing unit has a function of identifying whether or not a predetermined opening 32 of the catheter 30 is below the diaphragm.

The third information processing unit has a function of identifying whether or not a predetermined opening 32 of the catheter 30 is in a predetermined position or region of an alimentary canal. As the predetermined position of the alimentary canal, for example, a predetermined position of the stomach, the duodenum, the large intestine, and the small intestine can be listed. As the predetermined region of the alimentary canal, the region of an organ, such as the stomach, the duodenum, the large intestine, and the small intestine, or a partial region can be listed.

The fourth information processing unit has a function of identifying whether or not a predetermined opening 32 of the catheter 30 is in a predetermined position or region from the ureter to the bladder.

The processing in the information processing unit can be performed by a computer. The computer and the photographing unit 42 may be connected to each other, the information processing unit may process the photographed information photographed by the photographing unit 42, and the processed information may be displayed on the display device.

As a first aspect of a method of identifying the positions of the openings 32 of the catheter 30, there is a method that includes a step of inserting the catheter 30 according to the embodiment into the body, a step of causing the light sources 10 of the catheter 30 to emit light, and a step of photographing the light of the light sources 10 by the photographing unit 42.

As a second aspect of a method of identifying the positions of the openings 32 of the catheter 30, there is a method that include a step of inserting the catheter 30 according to the embodiment into the body, a step of causing the light sources 10 of the catheter 30 to emit light, and a step of receiving the light of the light sources 10 by the light receiving unit 46.

The first aspect and the second aspect may be combined.

The light sources 10 can be controlled by a control device 48. The control device 48 can be electrically connected to the light sources 10 via the wiring 36.

6. Internal Object Presence Determination Assistance Device

The opening position identification device 40 according to the embodiment can be applied as an object presence determination assistance device for determining whether or not a liquid material or a solid matter exists in an organ where the catheter 30 exists, such as the stomach or the intestines. It is possible to determine whether or not an object exists in the organ where the catheter 30 exists by photographing the light of the light sources 10 in the body, and based on the difference in at least one of the hue, brightness, and saturation of the photographed image, the difference in the amount of light of the light receiving unit 46, or the difference in illuminance. The content existing in the body may be grasped by transmission of the wavelength of the light.

7. Diagnostic Assistance Device

The opening position identification device 40 according to the embodiment can be used as a device that assists diagnosis of the state of a surface of an organ in the body where the catheter 30 exists, such as the stomach and the intestines, and a portion of the body between the surface and the skin. It is possible to grasp the state of the surface of the organ in the body where the catheter 30 exists, such as the stomach or the intestines, and the portion of the body between the surface and the skin, by photographing the light of the light sources 10 in the body, and based on the difference in at least one of the hue, brightness, and saturation of the photographed image, the difference in the amount of light of the light receiving unit 46, or the difference in illuminance.

When the light of the light sources 10 emit near infrared rays, oxyhemoglobin and deoxyhemoglobin may be measured, the near infrared rays that have passed through the body are detected by a detection device such as a light receiving element, and the oxygen concentration may be derived from the intensity of the transmitted wavelength.

The diagnostic assistance device can be applied to various diagnostic devices.

8. Treatment Assistance Device

The opening position identification device 40 according to the embodiment can be applied as a treatment assistance device that photographs the light sources 10 (including the light sources 10 of the guide wire 20) of the catheter 30 in the body by the photographing unit 42, and while recognizing the positions of the openings 32 with the light sources 10, kills cancer cells or reduces the activity of cancer cells through the light.

The treatment assistance device can be applied to various treatment devices.

9. Operations and Effects

Although it is conceivable to identify the position of the catheter 30 with the impedance of an electrode, the position of the catheter 30 can only be grasped as a relative position. Additionally, in the case of a magnetic sensor, a correct position cannot be grasped when the magnetic sensor is shifted.

According to the present embodiment, since the positions can be identified based on the light sources 10 of the catheter 30, the positions of the openings 32 can be accurately identified. Additionally, the positions of the openings 32 can be visually and easily grasped by displaying an image or a video obtained by photographing the light of the light sources 10 on the display device.

The present embodiment can be modified in various manners within the scope of the present invention.

INDUSTRIAL APPLICABILITY

The present invention can be applied to a catheter and various objects utilizing a catheter.

REFERENCE SIGNS LIST 10 light source
20 guide wire
30 catheter
32 opening
34 insertion facilitating member
36 wiring
40 opening position identification device
42 photographing unit
44 display device
46 light receiving unit
48 control device

The invention claimed is:

1. A guide wire to be inserted into a catheter having an opening for introducing a fluid substance into a body, or for sucking the fluid substance in the body, the catheter extending in an axial direction of the catheter, and the opening of the catheter facing in a radial direction around the axial direction of the catheter, which is perpendicular to the axial direction, wherein the guide wire, which extends in an axial direction of the guide wire, is provided with one or more light sources that are arranged along the axial direction of the guide wire from a distal end of the guide wire and a conducting wire that extends in the axial direction of the guide wire and is bundled with the guide wire to supply electric power to the light sources, wherein the light sources are configured to face in a radial direction around the axial direction of the guide wire such that, when one of the light sources of the guide wire meets the opening, and light emitted from the one of the light sources is transmitted through the opening outside the catheter, identifying a position of the opening of the catheter, and the guide wire is made of a material having less flexible than a material of the catheter such that, when the guide wire is inserted into the catheter, the catheter is more easily to travel straight through the body in comparison to the catheter without the guide wire.

2. A catheter into which the guide wire according to claim 1 is inserted.

3. The catheter according to claim 2, wherein
an end face of the tip of the catheter is configured opened, and
no light source is provided at the distal end of the guide wire such that light is not emitted from the end face of the opened tip.

4. An opening position identification device comprising:
the catheter according to claim 2; and
a photographing unit for photographing the light emitted from the light sources of the guide wire when the catheter is in the body to identify the position of the opening of the catheter.

5. The opening position identification device according to claim 4, further comprising:
a display device that displays information based on image information or video information photographed by the photographing unit.

6. The opening position identification device according to claim 4, further comprising:
a light receiving unit that receives the light of the light sources of the guide wire when the catheter is in the body.

7. The opening position identification device according to claim 4, further comprising:
an information processing unit, wherein
the information processing unit has a function of identifying whether or not a predetermined opening of the catheter is in a predetermined position or region of an alimentary canal.

8. A method of identifying a position of an opening of a catheter, the method comprising:

a step of inserting the catheter according to claim 2 into the body;
a step of causing the light sources of the guide wire to emit the light; and
a step of photographing the light of the light sources by a photographing unit.

9. A method of identifying a position of an opening of a catheter, the method comprising:
a step of inserting the catheter according to claim 2 into the body;
a step of causing the light sources of the guide wire to emit the light; and
a step of receiving the light of the light sources by a light receiving unit.

10. An object presence determination assistance device for assisting determination of whether or not an object exists in a predetermined portion or organ in a body, the object presence determination assistance device comprising the opening position identification device according to claim 4.

11. The guide wire according to claim 1, wherein
the catheter has a plurality of the openings that are arranged along the axial direction of the catheter at predetermined intervals from a tip of the catheter,
the guide wire has a plurality of the light sources that are arranged along the axial direction of the guide wire at predetermined intervals from the distal end of the guide wire, all facing the radial direction of the guide wire, and
the light sources are configured to be arranged such that, when one of the light sources of the guide wire, which is the closest to the distal end of the guide wire in the axial direction, meets one of the openings, which is the closest to the tip of the catheter, the lights emitted from the light sources are transmitted through the openings outside the catheter, identifying the position of the openings of the catheter.

12. The guide wire according to claim 1, wherein
the light sources emit the light with intensity so sufficient that the light transmitting through the opening penetrates the body and is seen outside the body.

13. The guide wire according to claim 1, wherein
the catheter is provided with an insertion facilitating member at the tip of the catheter, wherein
the insertion facilitating member has a rounded shape with a smooth protruding tip, having an outer diameter larger than an outer diameter of the catheter, and
the insertion facilitating member functions as a stopper for the guide wire such that the guide wire does not move farther beyond the insertion facilitating member in the axial direction.

14. The guide wire according to claim 13, wherein
the opening is provided with the insertion facilitating member, and
the guide wire has only the one light source at a tip of the guide wire.

15. The guide wire according to claim 1, wherein
the guide wire is to be pull out of the catheter before either introducing the fluid substance or sucking the fluid substance.

* * * * *